(12) United States Patent
Henderson et al.

(10) Patent No.: US 9,051,282 B2
(45) Date of Patent: Jun. 9, 2015

(54) METHODS FOR TRIAZOLE SYNTHESIS

(71) Applicant: CHEMTREAT, INC., Ashland, VA (US)

(72) Inventors: William H. Henderson, Ashland, VA (US); John Richardson, Hanover, VA (US)

(73) Assignee: CHEMTREAT, INC., Glen Allen, VA (US)

( * ) Notice: Subject to any disclaimer, the term of this patent is extended or adjusted under 35 U.S.C. 154(b) by 0 days.

(21) Appl. No.: 13/717,679

(22) Filed: Dec. 17, 2012

(65) Prior Publication Data
US 2014/0171658 A1   Jun. 19, 2014

Related U.S. Application Data

(60) Provisional application No. 61/576,822, filed on Dec. 16, 2011.

(51) Int. Cl.
*C07D 249/18*   (2006.01)
(52) U.S. Cl.
CPC .................................. *C07D 249/18* (2013.01)
(58) Field of Classification Search
CPC ..................................................... C07D 249/18
USPC ........................................................ 548/257
See application file for complete search history.

(56) References Cited

U.S. PATENT DOCUMENTS 3,564,001 A * 2/1971 Long, III ........................ 548/257
4,299,965 A * 11/1981 Chan et al. ..................... 548/257

OTHER PUBLICATIONS

Wiley, Essential Biochemistry, 2004, John Wiley & Sons.*

* cited by examiner

*Primary Examiner* — Rebecca Anderson
*Assistant Examiner* — Karen Cheng
(74) *Attorney, Agent, or Firm* — Oliff PLC

(57) ABSTRACT

Disclosed are methods of synthesizing triazoles that avoids the use of concentrated acids in favor of carbonic acid generated from $CO_2$ that can be practiced at ambient and/or elevated temperature and/or atmospheric and/or elevated pressures. The disclosed methods also provide a way of synthesizing triazole products that are sufficiently pure and/or of sufficient concentration whereby the reaction product(s) may not require purification or other treatment before being used in, for example, formulating water treatment compositions that will tend to suppress corrosion or as an intermediate product in a more complex synthesis.

7 Claims, No Drawings

METHODS FOR TRIAZOLE SYNTHESIS

PRIORITY STATEMENT

This application claims priority under 35 U.S.C. §119(e) from U.S. Provisional Application No. 61/576,822, filed Dec. 16, 2011, the contents of which are incorporated, by reference, in their entirety.

FIELD OF THE INVENTION

The invention relates to a new method for synthesizing triazoles through the diazotization of amines, more particularly methods for synthesizing 1,2,3-triazoles from diamines including, for example, benzotriazole (BZT) and other derivatives, that avoids the use of strong acids, metal catalysts based on, for example, Cu, Ag, Rh and/or Pd, and, at least with respect to some applications, can reduce or eliminate the need for additional concentration and/or purification of the reaction product(s) before subsequent use or additional processing.

BACKGROUND OF THE INVENTION

As a class, triazoles have shown a wide range of utility, particularly in the formulation of antifungal drugs for treating mammalian afflictions including, for example, fluconazole, isavuconazole, itraconazole, voriconazole, pramiconazole, and posaconazole as well as antifungal compositions for agricultural applications including, for example, epoxiconazole, triadimenol, propiconazole, metconazole, cyproconazole, tebuconazole, flusilazole and paclobutrazol.

Prior art references disclose several diazotization procedures for preparing such compounds. Generally, an amine is reacted with nitrous acid, which is generated by the addition of a mineral acid or an organic acid. Most commonly, an excess of sulfuric, hydrochloric, or acetic acid is used to generate in situ the nitrous acid used in the diazotization reactions. This acidic medium must be disposed of or stored once the reaction is complete. These reactions are maintained at temperatures typically ranging from 0° C. to 50° C. In the case of triazole synthesis, filtration and drying or distillation steps are typically required in order to isolate the target triazole(s) before dissolving the triazole product(s) in either a basic aqueous solution or a highly acidic aqueous solution. These additional steps can prove both costly and time consuming in terms of manufacturing.

It is an object of the present invention to provide improved methods for the diazotization of amines capable of producing a range of triazole compounds that can be used as final products or as intermediates in more complex synthesis processes that is both simplifies the synthesis operation and avoids the use of strong acids.

It is another object of this invention to provide methods for the direct synthesis of triazole compounds of sufficient purity and concentration directly in an aqueous solution and thereby reduce or eliminate the need for subsequent isolation, concentration, neutralization and/or purification procedures, thereby both reducing the complexity of the process and reducing or eliminating the need to dispose of any related aqueous or organic waste.

Additionally, it is an object of this invention to provide methods using carbon dioxide and water to form carbonic acid in concentrations sufficient to result in the formation of nitrous acid.

These and other objects of the present invention are accomplished by the methods and examples detailed below in which appropriate amine(s), nitrite salt(s) and carbon dioxide are dissolved in an aqueous reaction solution and reacted to produce the target triazole(s).

Those of ordinary skill in the art will appreciate that BZT is widely used as a copper and/or yellow metal corrosion inhibitor, as an intermediate or primary compound in the synthesis of dyes, fungicides and plant growth regulators, and as a polymerization catalyst. Consequently, a number of BZT synthesis procedures have been developed over the years, typically involving a diazotization reaction in which a nitrite salt, typically orthophenylenediamine (OPD), and an acid are mixed in an aqueous system and allowed to react for a substantial period of time. Certain of these synthesis procedures have been the subject of previous U.S. Patents including, for example, U.S. Pat. Nos. 2,861,078; 3,227,726; 3,334,054; 3,564,001 and 4,299,965, the contents of which are incorporated, in their entirety, by reference.

In many instances, however, the product(s) of these synthesis procedures are impure and/or of lesser quality than desired. Accordingly, in many instances the initial BZT product must be subjected to additional processing including, for example, further processing by carbon treatment, crystallization and/or distillation processing steps, thereby increasing both the time and expense of preparing a suitable BZT composition. In addition, certain of these methods are typically run at relatively low solids concentrations and can, for example, result in an initial product that has a relatively low BZT content of, for example, less than 15% in the final reaction mixture.

Accordingly, it is an object of the present invention to provide a method for the preparation of BZT and other triazoles and their derivatives that is less expensive, relatively simple, more ecologically friendly than those presently available capable of producing sufficiently pure triazole product(s) whereby additional purification steps are not required.

As disclosed in U.S. Pat. No. 4,299,965, for example, an aqueous mixture of orthophenylenediamine and acetic acid is slowly added to a cooled sodium nitrite solution after which the reaction represented below in Formula [1] is allowed to proceed for a period of about one to three hours. The reaction mixture will have a concentration of from about 12 wt % to 22 wt % of active ingredients. It is suggested that the order in which the reagents is added is not important, so long as one reagent is being added to the other at a rate sufficiently so as to keep the temperature of the reaction mixture below about 25° C.

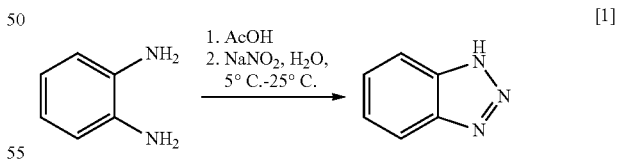

[1]

The reaction step is then followed by neutralization step using sodium hydroxide to increase the pH of the reaction mixture to 6 to 6.5, with the reaction and neutralization steps being achieved at relatively low temperatures, typically between 5° C. and 25° C. A precipitate of BZT is formed, filtered and washed with cold water to yield technical grade product suitable for use in industrial applications. The relative aqueous concentrations of the reactants is preferably adjusted to give 15 to 25 wt % of the BZT product, a mole ratio of 0.9 to 1.1 for orthophenylenediamine to sodium nitrite and a mole ratio of 1.8 to 2.2 for acetic acid to orthophenylenediamine.

The amount of caustic used in the neutralization must be less than about 0.8 moles per mole of acetic acid.

Similar prior art synthesis methods have used other strong acids including, for example, sulfuric acid, to achieve a result similar to that obtained with the acetic acid. The reactions utilized in other methods of synthesizing BZT are illustrated below in general Formula [2] and example Formulae [3]-[5].

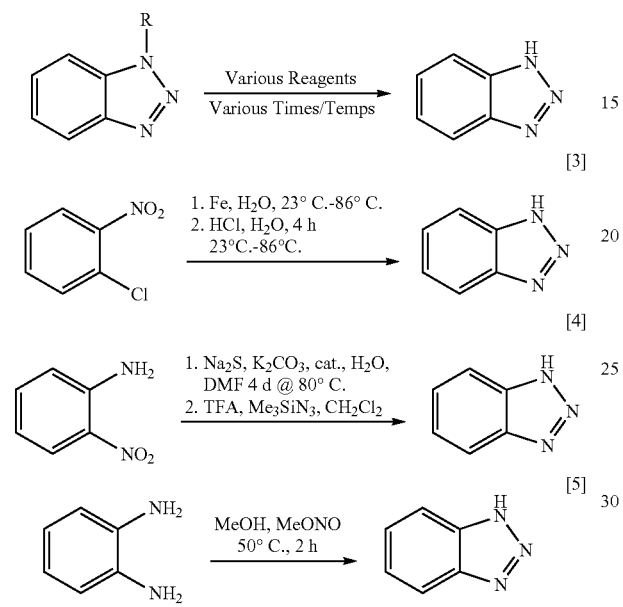

BRIEF SUMMARY OF THE INVENTION

The method according to the present disclosure provides a way of synthesizing triazoles that avoids the use of concentrated acids, avoids the use of excessive acid (and the counterpart caustic addition necessary to increase the pH of the reaction product in such synthesis methods), can be practiced at ambient and/or elevated temperature and/or atmospheric and/or elevated pressures. Further, the methods according to the present disclosure can provide a way of synthesizing triazole products that are sufficiently pure and/or of sufficient concentration whereby the reaction product(s) does not require purification or other treatment before being used in, for example, formulating water treatment compositions that will tend to suppress corrosion or as the intermediate solution in a more complex synthesis.

DETAILED DESCRIPTION

Using a BZT synthesis as an example, the basic reaction as reflected in Formula [6] can utilize $CO_2$ bubbled through the reaction mixture or introduced into a head space above the reaction mixture to establish an equilibrium concentration of $CO_2$ relative to $H_2CO_3$ in the reaction mixture. The $H_2CO_3$ and $NaNO_2$ are, in turn, in equilibrium with $HNO_2$ and $NaHCO_3$ as illustrated in Formulae [7] and [8] with the $HNO_2$ reacting with the phenylenediamine to produce the desired BZT.

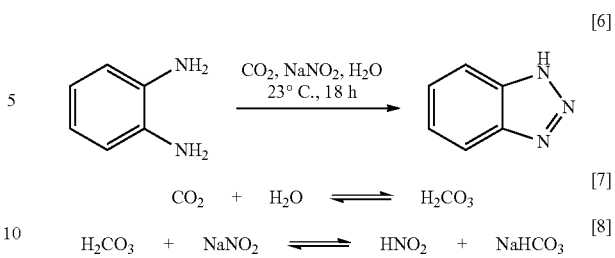

EXAMPLES

Example 1

A reactor was charged with o-phenylenediamine (51.5 g, 0.476 mol, 1.00 equiv). A 40% aqueous solution of $NaNO_2$ (88 mL, 0.670 mol, 1.40 equiv) was added and $CO_2$ (1 atm) bubbled into the reactor. The solution was stirred for 22 h at ambient temperature. $H_2O$ (50 mL) was added and the solution stirred for an additional 7 h at ambient temperature. The yield of benzotriazole was determined to be 95-100% by a Hach triazole test.

Example 2

A reactor was charged with o-phenylenediamine (90.6 g, 0.838 mol, 1.00 equiv), a 40% aqueous solution of $NaNO_2$ (117 mL, 0.889 mol, 1.06 equiv) and $H_2O$ (115 mL). $CO_2$ (1 atm) was bubbled into the reactor and the solution was stirred for 20 h at ambient temperature. The yield of benzotriazole was determined to be 95-100% by a Hach triazole test.

Example 3

A reactor was charged with o-phenylenediamine (45.45 g, 0.420 mol, 1.00 equiv) and $H_2O$ (50 mL). $CO_2$ (1 atm) was bubbled into the reactor while the solution was warmed to 35° C. A 40% aqueous solution of $NaNO_2$ (58 mL, 0.440 mol, 1.05 equiv) was added and the solution stirred for 17 h. The yield of benzotriazole was determined to be 92-99% by a Hach triazole test.

Example 4

A reactor was charged with o-phenylenediamine (45.6 g, 0.422 mol, 1.00 equiv), a 40% aqueous solution of $NaNO_2$ (58 mL, 0.442 mol, 1.05 equiv) and $H_2O$ (50 mL). The solution was heated to 70° C. as $CO_2$ (1 atm) was bubbled into the reactor. The solution was stirred for 20 h at 70° C. for 16 h. The solution was then heated to 80-85° C. to expel $CO_2$ and the resulting reaction mixture used to make an alkaline BZT solution. The yield of benzotriazole was determined to be 95-100% by a Hach triazole test.

Example 5

A reactor was charged with o-phenylenediamine (45.4 g, 0.420 mol, 1.00 equiv), a 40% aqueous solution of $NaNO_2$ (57 mL, 0.434 mol, 1.03 equiv). The solution was heated to 65° C. as $CO_2$ (1 atm) was bubbled into the reactor. The solution was stirred for 16 h at 65° C. for 16 h. The solution was then heated to 80-85° C. to expel $CO_2$ and the resulting reaction mixture used to make an alkaline BZT solution. The yield of benzotriazole was determined to be 95-100% by a Hach triazole test.

The basic synthesis process as illustrated in Formula [6] may be conducted at elevated temperatures, in a pressure vessel and/or more actively stirred with the reaction rate tending to increase accordingly, but such modifications will tend to increase the expense associated with the synthesis. Another variation of the basic synthesis process comprises terminating the $CO_2$ flow and heating the reaction mixture near the end of the process in order to drive off additional $CO_2$ and thereby obtain a more concentrated BZT solution (due to the reduced concentration of $NaHCO_3$ present in the reaction mixture).

Example 6

A 500 mL round-bottomed flask was charged with o-phenylenediamine (45.73 g), sodium nitrite (40% aq, 57 mL) and water (70 mL). The solution was purged with $CO_2$ using a subsurface tube and heated to 55° C. Carbon dioxide was bubbled through the solution with stirring for 20 h before the CO2 feed was removed and the reaction opened to the atmosphere. The solution was then heated to 90 C for 3 h where it slowly turned from milky brown to a clear deep brown mixture. Potassium hydroxide (20 mL) was then added in three portions and the solution cooled to room temperature. The % 1,2,3-benzotriazole was determined to be 24.6% by HPLC.

Example 7

A 5 L round-bottomed flask was charged with o-phenylenediamine (1.081 kg), sodium nitrite (40% aq, 1.355 L) and water (1.00 L). The solution was purged with carbon dioxide and then heated to 75° C. for 8 h under a $CO_2$ atmosphere with stifling. After the reaction was complete, the $CO_2$ subsurface tube was removed, the reaction was opened to the ambient atmosphere and the solution heated to 90° C. for 3 h. Potassium hydroxide was added along with additional water (175 mL). The deep brown solution was determined to be 24.3% 1,2,3-benzotriazole by HPLC.

Example 8

A 350 mL pressure vessel was charged with o-phenylenediamine (45.56 g), sodium nitrite (40% aq, 57 mL) and water (50 mL). The vessel was purged three times by pressurizing with carbon dioxide and releasing the pressure. Once the purge was complete, the vessel was pressurized to 60 psi using $CO_2$ and heated to 150° C. for 3 h. After the reaction was complete the pressure was released and the solution refluxed for 30 min. After refluxing the solution was cooled and potassium hydroxide added. The yield of benzotriazaole was determined to be 95-100%.

Benzotriazole is known for its great versatility. It has already been used as a restrainer in photographic emulsions and as a reagent for the analytical determination of silver. More importantly, it has been extensively used as a corrosion inhibitor in the atmosphere and underwater. Also, its derivatives and their effectiveness as drug precursors have been drawing increasing attention. Besides all the application mentioned above, the BTA can be used as antifreezes, heating and cooling systems, hydraulic fluids and vapor phase inhibitors as well.

Benzotriazole is an effective corrosion inhibitor for copper and its alloys by preventing undesirable surface reactions. It is known that a passive layer, consisting of a complex between copper and benzotriazole, is formed when copper is immersed in a solution containing benzotriazole. The passive layer is insoluble in aqueous and many organic solutions. There is a positive correlation between the thickness of the passive layer and the efficiency of preventing corrosion. The exact structure of the copper-BTA complex is controversial and many proposals have been suggested.

Benzotriazole derivatives have chemical and biological properties that are versatile in the pharmaceutical industry. Benzotriazole derivatives act as agonists for many proteins. For instance, vorozole and alizapride have the inhibitory properties against different proteins and benzotriazole esters have been reported to work as mechanism-based inactivators for severe acute respiratory syndrome (SARS) 3CL protease. The methodology is not only limited to heterocyclization but was also successful for polynuclear hydrocarbons of small carbocyclic systems.

Benzotriazole is fairly water-soluble, not readily degradable and has a limited sorption tendency. Hence, it is only partly removed in wastewater treatment plants and a substantial fraction reaches surface water such as rivers and lakes.

As will be appreciated by those of ordinary skill in the art, the basic synthesis process as illustrated in Formula [6] may be used for synthesizing other triazole compounds and derivatives from a variety of aliphatic diamines and aromatic diamines as reflected below in Formula [9] for the formation of BZT derivatives from OPD and Formulae [10] and [11] for examples of other linear and branched aliphatic diamine derivatives:

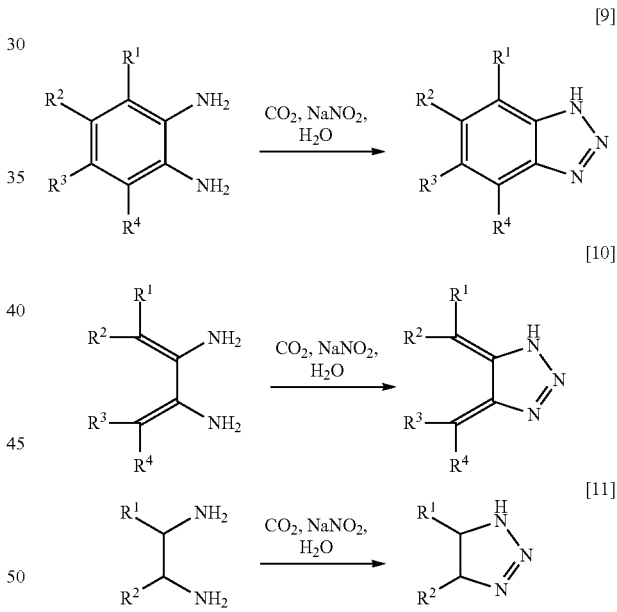

wherein R1, R2, R3 and R4 are independently selected from a group consisting of hydrogen, halogens, amino, alkyl, aryl and vinyl groups.

One skilled in the art will appreciate various modifications can be made to the teachings of the present disclosure without departing from the intended spirit and scope thereof. It is intended that the inventions disclosed herein be limited only by the terms of the appended claims.

We claim:
1. A method for synthesizing a 1,2,3-triazole compound in an aqueous solution comprising:
  forming an aqueous solution of a diamine and a nitrite salt;
  introducing carbon dioxide into the aqueous solution to form carbonic acid;

reacting a portion of the carbonic acid with the nitrite salt to produce nitrous acid and a bicarbonate; and reacting the diamine with a portion of the nitrous acid for a reaction period at a reaction pressure and a reaction temperature sufficient to produce the 1,2,3-triazole compound.

2. The method for synthesizing a 1,2,3-triazole compound according to claim 1, wherein:
the reaction pressure is within a range of from 1 atm to 4 atm.

3. The method for synthesizing a 1,2,3-triazole compound according to claim 1, wherein:
the reaction temperature is within a range of from 0° C. to 150° C.

4. The method for synthesizing a 1,2,3-triazole compound according to claim 1, wherein:
at least about 80% of the diamine is converted to the 1,2,3-triazole compound.

5. A method for synthesizing a 1,2,3-triazole compound in an aqueous solution comprising:
forming an aqueous solution of an aromatic diamine and a nitrite salt;
introducing carbon dioxide into the aqueous solution to form carbonic acid;
reacting a portion of the carbonic acid with the nitrite salt to produce nitrous acid and a bicarbonate; and
reacting the aromatic diamine with a portion of the nitrous acid for a reaction period at a reaction pressure and a reaction temperature sufficient to produce the 1,2,3-triazole compound.

6. The method for synthesizing a 1,2,3-triazole compound according to claim 5, wherein:
the aromatic diamine is orthophenylenediamine.

7. The method for synthesizing a 1,2,3-triazole compound according to claim 5, wherein:
the aromatic diamine is an orthophenylenediamine derivative represented by the formula

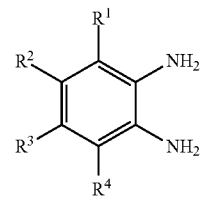

wherein $R^1$, $R^2$, $R^3$ and $R^4$ are independently selected from a group consisting of hydrogen, halogens, amino, alkyl, aryl and vinyl groups.

* * * * *